United States Patent [19]

Sims

[11] 4,281,171

[45] Jul. 28, 1981

[54] LIQUID CARBON DIOXIDE EXTRACTION OF PYRETHRINS

[76] Inventor: Marc Sims, 5835 Colton Blvd., Oakland, Calif. 94611

[21] Appl. No.: 60,886

[22] Filed: Jul. 26, 1979

[51] Int. Cl.$^3$ ............................................. C07C 67/48
[52] U.S. Cl. .................................................. 560/124
[58] Field of Search ....................................... 560/124

[56] References Cited

U.S. PATENT DOCUMENTS

| | | | |
|---|---|---|---|
| 1,595,538 | 8/1926 | Yamamoto | 560/124 |
| 1,786,967 | 12/1930 | Trevillian | 560/124 |
| 1,915,662 | 6/1933 | Gnadinger | 560/124 |
| 2,050,974 | 8/1936 | La Forge | 560/124 |
| 2,056,438 | 10/1936 | Ward | 167/24 |
| 2,372,183 | 3/1945 | Barthel | 560/124 |
| 2,376,702 | 5/1945 | Komeda | 560/124 |
| 2,413,107 | 12/1946 | Kuhn | 560/124 |
| 2,449,671 | 9/1948 | Rhodes | 560/124 |
| 2,467,859 | 4/1949 | Sankowsky | 560/124 |
| 3,042,706 | 7/1962 | Haus | 560/124 |
| 3,083,136 | 3/1963 | Levy | 424/305 |
| 3,333,962 | 8/1967 | Prebluda | 99/2 |
| 3,835,776 | 9/1974 | Mutsuo | 560/124 |
| 3,862,174 | 1/1975 | Mizutani | 560/124 |
| 3,894,073 | 7/1975 | Alexander | 560/124 |
| 3,973,036 | 8/1976 | Hirano | 424/304 |
| 4,012,194 | 3/1977 | Maffel | 8/742 |
| 4,024,163 | 5/1977 | Elliott | 260/347.4 |

FOREIGN PATENT DOCUMENTS 702886  1/1954  United Kingdom ............... 560/124

OTHER PUBLICATIONS

Sax, "Dangerous Properties of Industrial Materials," 5th Ed., pp. 756 & 863 (1979).
Casida, "Pyrethrum the Natural Insecticide," pp. 25–53 (1973).
Schultz, Food Technology, 24, pp. 94–98 (1970).

Primary Examiner—Natalie Trousof
Assistant Examiner—Michael Shippen
Attorney, Agent, or Firm—Cushman, Darby & Cushman

[57] ABSTRACT

Pyrethrum flowers are extracted with liquid carbon dioxide in suitable equipment to yield a pale, transparent, concentrated extract of pyrethrins. The extract is useful as the active material in safe insecticidal formulations. Alternatively, crude oleoresin produced by extraction of pyrethrum with organic solvents can also be purified by treatment with liquid carbon dioxide.

4 Claims, 1 Drawing Figure

LIQUID CARBON DIOXIDE EXTRACTION OF PYRETHRINS

BACKGROUND OF THE INVENTION

It has been known for centuries that the pyrethrum flower has insecticidal value. The flower was originally used in the form of a powder, but more recently the preferred form of use is as a liquid which contains an extract of the flower. It has been found that the insecticidal property of the pyrethrum flower is due primarily to five esters, the pyrethrins I and II, the cinerins I and II, and jasmolin II. Collectively these compounds are called the pyrethrins. Accordingly, for the purposes of the specification and the claims which follow, the term, pyrethrin, is intended to connote the above esters, either singly or as a collective mixture.

The pyrethrins, when used in effective insecticidal amounts, are very effective in killing many types of insects with the advantage of having low mammalian toxicity. They are extremely unstable to light, oxidation, and heat and this prevents persistent residues from accumulating. The lack of persistance has also prevented insects from adapting a resistance to the pyrethrins. However, the instability poses problems in processing flowers to a refined concentrate without causing excessive degradation loss of pyrethrin activity.

The pyrethrins are soluble in a wide range of organic solvents such as benzene, hexane, petroleum ether, alcohol, acetone, chlorinated hydrocarbons, etc. The pyrethrins can be extracted commercially in conventional solids leaching equipment with a suitable organic solvent. Although the pyrethrins are soluble in many solvents, practical considerations limit the selection to only a few. There are several important qualities to consider in the choice of solvent.

One desirable quality is that the solvent should be as selective as possible toward the pyrethrins, that is, it should dissolve all the pyrethrins without completely dissolving all the other natural constituents such as water, pigments, waxes, fatty acids, etc., which represent contaminants and must be removed as nearly as is feasible by further purification processes.

Another desirable quality is that the solvent must be volatile enough so that it can be stripped from the concentrate to a low percentage without the need for heating to an elevated temperature. This is important because degradation of insecticidal activity will occur with prolonged heating. Therefore, the solvent should have as low a boiling point as is feasible. Preferably, the temperature of the concentrate should not be raised at all, but a thin-film vacuum stripper may then be required to achieve adequate rates of volatilization at ambient temperature. Even when using a solvent with a relatively low boiling point such as hexane, thin-film vacuum stripping will still be required to achieve a low concentration of residual hexane in the concentrate. It is also important for economic reasons that the solvent be easy to volatilize so that it can be recovered for recycling and does not add to the shipping weight of concentrate.

A further desirable quality is that the solvent should be inexpensive and available in larger supply.

Yet another desirable quality is that the solvent should be safe toward personnel and environment. Preferably, it would be non-toxic, non-corrosive, non-reactive, and non-flammable.

A number of solvent extraction procedures have been proposed for obtaining pyrethrins as evidenced by U.S. Pat. Nos. 2,056,438; 3,083,136 and 3,333,962.

In a typical prior art process hexane is used to leach the ground dried flowers. The extraction is more efficient if the hexane or other organic solvent is heated above ambient temperature, the upper limit being its boiling point. However, raising the temperature also accelerates degradation loss of the pyrethrins. The hexane is then removed to as low a concentration as is feasible by heating the extract under partial vacuum to yield a dark, viscous oleoresin. The typical concentration of pyrethrins in the oleoresin is 30% by weight with the contaminants consisting primarily of fatty acids, alkanes, triterpenols, sterols, and the pigments chlorophyll and carotenoids. Most of the production of pyrethrum extract is used in household aerosol sprays, and for this application the color must be removed to avoid spotting. Also it has been found that the pigments and other reactive constituents of the extract promote degradation of the pyrethrins in storage. Another purification step is therefore required which will yield a pale transparent concentrate.

Typically purification consists of dissolving the oleoresin in methanol followed by precipitation of the contaminants or charcoal filtration. The methanol must then be stripped from the concentrate unless it can be tolerated in the insecticidal formulation. Molecular distillation and precipitation from Freon solution have also been used to purify the extracts.

All of the purification processes generate substantial quantities of waste material which pose a disposal problem. The wastes include waxy colored residues, filter aids, and decolorizing adsorbents.

As a result, despite the excellent usefulness of pyrethrins, due to the relatively high costs of obtaining same, efforts have been made to develop synthetic substitutes as evidenced by U.S. Pat. Nos. 3,385,176; 3,862,174; 3,973,036 and 4,024,163. Unfortunately, the synthetic alternatives have not been altogether effective from both an insecticidal as well as economic viewpoint.

Thus, there is a need in the art to develop an improved method of removing pyrethrins from the material which contain them.

Accordingly, it is a primary object of the present invention to provide a relatively simple and economical means for the extraction of pyrethrins.

It is also an object of the present invention to provide a means of obtaining pyrethrins in a relatively pure and stable state.

These and other objects of the present invention will be more apparent from the discussion which follows.

SUMMARY OF THE INVENTION

According to the present invention, it has been discovered that it is possible and economically worthwhile to use liquid carbon dioxide as a solvent to extract pyrethrins from pyrethrum in suitable solids leaching equipment. The process eliminates most of the problems associated with the use of organic solvents.

Under pressure, carbon dioxide exists as a saturated liquid in the temperature range of $-56°$ to $31°$ C. ($-69°$ to $88°$ F.) and corresponding pressure range of 5 to 73 bar. Liquid carbon dioxide has unique solvent properties. Oxygenated organic compounds with low to medium molecular weights, i.e. less than 500 Daltons, such as those with ester, ether, aldehyde and/or ketone functional groups are very soluble in liquid carbon dioxide. Water, fatty acids, higher alkanes, sterols, and triterpenols are constituents of pyrethrum which are only partially soluble in liquid carbon dioxide. Other pyrethrum constituents such as sugars, inorganic salts, fruit acids, alkaloids, amino acids, and the pigments chlorophyll and carotenoids are insoluble in liquid carbon dioxide. Since the pyrethrin molecules contain one ketone and one or two ester groups, the remainder of the molecule being hydrocarbon, they should be very soluble in liquid carbon dioxide.

Liquid carbon dioxide has been used heretofore in the extraction of aroma constituents of fruit juices and coffee as described by Schultz et al, "Liquid Carbon Dioxide for Selective Aroma Extraction," Food Technology, Vol. 24, No. 11, pages 94-98 (1970), and also for dry cleaning as set forth in U.S. Pat. No. 4,012,194.

In addition to the unique solvent characteristics of liquid carbon dioxide, it is noted that pyrethrum flowers and organic solvent extracts derived therefrom are complex chemical mixtures containing numerous components. Thus, when these components, having various degrees of solubility, are contacted with liquid carbon dioxide, an extract of unique chemical composition is formed.

DETAILED DESCRIPTION OF THE INVENTION

Figure 1:
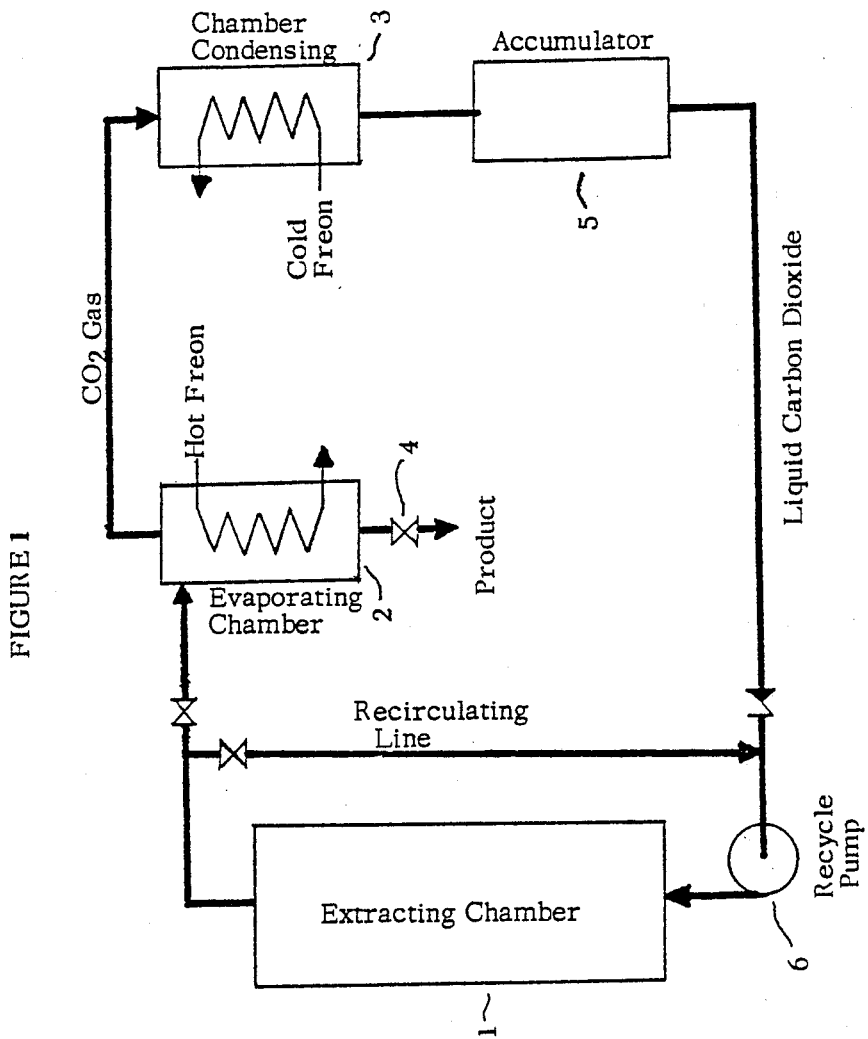

The process of the present invention is generally illustrated in FIG. 1. Ground pyrethrum is loaded into the extracting chamber 1 and liquid carbon dioxide is percolated through the bed of pyrethrum, the flow being either upward (shown) or downward. The stream of liquid carbon dioxide and solutes passes into the evaporating chamber 2 where heat is applied to boil the liquid carbon dioxide, converting it to gaseous carbon dioxide which passes to the condensing chamber 3. Since the solutes are predominantly non-volatile at the conditions in the evaporating chamber, they accumulate and are withdrawn through the product valve 4. Purified liquid carbon dioxide passes to the accumulator 5 from where it is recycled to the extracting chamber via the recycle pump 6.

The process of the present invention possesses a number of important advantages over normal organic solvent extraction. One advantage is that the product is a pale transparent concentrate of pyrethrins obtained in one step rather than two. Thus, a purification step is not required. This improved efficiency is due primarily to the selectivity of liquid carbon dioxide as a solvent for pyrethrins.

Another advantage is that the degradation loss of pyrethrin activity is minimized. The leaching is done at relatively low temperature in the range $-56°$ C. to $31°$ C., air and light are excluded from the process, and liquid carbon dioxide is inert toward the pyrethrins. Also, there is no intermediate handling and exposure to air since there is only one step.

Yet another advantage is that the final product is essentially a solvent-free concentrate. The vapor pressure of carbon dioxide is high relative to organic solvents, and once the product is released to atmospheric pressure only a trace of carbon dioxide will remain. Elimination of residual solvent reduces the shipping weight of product and therefore the shipping cost. It also avoids problems of incompatibility of residual solvent with the insecticidal formulation.

A further advantage is that no organic solvents will remain in the leached pyrethrum. It will contain only a trace of carbon dioxide which is inconsequential. The vegetable matter will be immediately available for further use with no need for solvent removal, e.g. as cattle feed.

A still further advantage is that the process of the present invention is more economical than prior art methods. Much of the economy is due to the replacement of two steps with one and the reduced degradation loss of pyrethrins. Although the equipment must be more robust than conventional leaching equipment to handle working pressures of 5 to 73 bar, there are substantial advantages that will offset the higher cost of pressure vessels and lines. Stripping carbon dioxide from the product is considerably easier than stripping solvents such as hexane, acetone, methanol, etc., and this eliminates the need for thin film evaporators and vacuum equipment with their large energy and space requirements. Vaporizing and condensing carbon dioxide for recycling requires little energy, partly because it can be done at ambient temperature near the critical point where the heat of vaporization approaches zero, and partly because it is easy to use a heat pump system to supply the heat of vaporization from heat recovered in the condenser. The small energy input can then be supplied electrically and no steam will be required. Makeup carbon dioxide represents a minor part of processing cost since carbon dioxide is comparatively cheap and available in large supply.

Yet a further advantage is that, although the pressure requires certain safety features, with these features the new process will be safer overall than a conventional extraction process. Unlike most organic solvents such as hexane, acetone, methanol, etc., carbon dioxide is non-flammable and no provisions need be made for a fire hazard. Carbon dioxide is also practically inert, non-corrosive, and non-toxic. Venting carbon dioxide poses almost no hazard to personnel or the environment. Cleanliness is easy to maintain since the equipment is enclosed and spills evaporate immediately.

According to an alternative embodiment of the present invention, the process of the present invention could be used to replace conventional oleoresin purification processes. All the advantages given above except for the replacement of two steps with one would apply. Using the liquid carbon dioxide process to purify oleoresin may be desirable in the event, for example, that oleoresin was in greater supply than pyrethrum flowers. To use the process illustrated in FIG. 1 for oleoresin purification, the oleoresin is mixed with liquid carbon dioxide in extracting chamber 1. After equilibration the waxy colored insoluble contaminants are removed, e.g. by filtration, and the liquid carbon dioxide containing dissolved pyrethrins is fed into the evaporating and recycling system of FIG. 1.

The following examples are offered to more fully illustrate the present invention, but are not to be construed as limiting the scope thereof.

EXAMPLE I

Finely ground dried pyrethrum, labelled Prentox Pyrethrum Powder 0.9, was obtained from the Prentiss Drug and Chemical Company. The extracting chamber was loaded with 5270 grams (11.6 pounds) of the pyrethrum powder, sealed, and evacuated. Carbon dioxide was introduced to the chamber until the bed of pyrethrum was submerged in 18.2 kilogram (40.1 pounds) of saturated liquid. Mass transport was promoted by withdrawing liquid from the bottom outlet and returning it to the top of the chamber via a pump. The liquid movement was maintained for 4 hours at a rate of 600 milliliters per minute. During this period the temperature ranged from 17° to 20° C. with corresponding saturated gas pressures of 53 to 56 bar. The liquid carbon dioxide stream was then pumped to the evaporator where in a period of one hour all the liquid carbon dioxide was boiled off, condensed, and collected in an accumulator. During the evaporation the entire system was isobaric at the saturated conditions of 20° C. and 56 bar. The heat of vaporization was supplied by hot Freon circulating in a heating jacket that surrounded the evaporating chamber. The heat was recovered from condensing carbon dioxide by expanding liquefied Freon, formed in the heating jacket, into a coil in the condensing chamber. The Freon is recycled by compressing it and feeding it back to the heating jacket. After all the liquid carbon dioxide was boiled away the temperature of the extract in the bottom of the evaporating chamber was allowed to rise to 30° C., the pressure was slowly released, and 51.0 grams of pale transparent product was drained into a bottle. Another 17.5 grams of product was obtained by washing the evaporating chamber with acetone and gently evaporating. The total weight of 68.5 grams of extract corresponds to a yield of 1.30% by weight.

EXAMPLE II

Using the same procedure and material as in Example I, 6370 grams of pyrethrum powder was submerged in 21.2 kilograms of liquid carbon dioxide which was pumped from the bottom of the extracting chamber to the top at a rate of 600 milliliters per minute for 6 hours. The temperature ranged from 16° to 19° C. The liquid carbon dioxide was evaporated in a one hour period at 19° C. to obtain 98.5 grams of pale transparent product directly from the evaporating chamber and another 16.8 grams from evaporation of the acetone wash solution. The total weight of 115.3 grams of extract corresponds to a yield of 1.81% by weight.

The pyrethrin content of the pyrethrum powder was determined by extracting a weighed portion of powder with methanol in a Soxhlet extractor. The procedure was repeated using hexane so that the efficacy of the two solvents for extracting pyrethrins could be compared. An aliquot of each extract was diluted prior to the final pyrethrin determination.

The quantity 51 milligrams of the extract prepared in Example II (not including the wash) was dissolved in 51 milliliters of xylene resulting in a 1.0 mg/ml solution. An aliquot of this solution was diluted with hexane prior to the final determination.

Final determination of the extracts was by gas chromatography using a Hewlett-Packard 5713 gas chromatograph equipped with an electron capture detector and a 3% OV-225/Chromosorb W column. The standard solution of pyrethrins was prepared from an analytical standard provided by the U.S. Environmental Protection Agency (Lot No. 7379, 21% purity). The results are shown in Table 1.

TABLE 1

| Sample | Percent Pyrethrins by Weight |
|---|---|
| Extract produced according to Example II | 47 ± 3 in extract |
| Pyrethrum powder (methanol extraction) | 0.8 ± 0.1 in powder |
| Pyrethrum powder (hexane extraction) | 0.6 ± 0.1 in powder |

The total available yield of extract which would contain 47% pyrethrins is calculated to be 1.70±0.21% using the methanol-determined pyrethrin content of the pyrethrum. The actual yield of extract containing 47% pyrethrins produced in Example II was 1.81% which indicates that pyrethrins removal was virtually complete.

Comparing the pyrethrin contents of the powder as determined by extracting with the two solvents indicates that under laboratory conditions hexane is not the best solvent with which to make the first extraction of ground dried pyrethrum.

While certain representative embodiments and details have been shown for the purpose of illustrating the invention, it will be apparent to those skilled in the art that various changes and modifications may be made therein without departing from the spirit or scope of the invention. It will further be understood that the invention may comprise, consist essentially of or consist of the steps or materials recited herein.

What is claimed is:

1. A process for removing pyrethrins from a pyrethrin containing material comprising the steps of:
   (i) contacting said pyrethrin containing material with liquid carbon dioxide; and
   (ii) separating said liquid carbon dioxide containing extracted pyrethrins from said material.

2. A process according to claim 1 which further comprises the step of:
   (iii) evaporating carbon dioxide from said liquid carbon dioxide containing extracted pyrethrins.

3. A process according to claim 2 which further comprises the steps of:
   (iv) reliquefying said evaporated carbon dioxide; and
   (v) contacting said reliquefied carbon dioxide with a pyrethrin containing material.

4. A process according to claims 1, 2 or 3, wherein said pyrethrin containing material is selected from the group consisting of pyrethrum flowers, oleoresins containing pyrethrins, and finely ground, dried pyrethrum.

* * * * *